(12) United States Patent
Siciliano et al.

(10) Patent No.: US 8,183,059 B2
(45) Date of Patent: **\*May 22, 2012**

(54) DEVICE FOR DETECTION OF TARGET MOLECULES AND USES THEREOF

(75) Inventors: Nicholas A. Siciliano, Cherry Hill, NJ (US); Martin Joseph Bouliane, Carlsbad, CA (US)

(73) Assignee: Invisible Sentinel, Inc., Philadelphia, PA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 13/221,116

(22) Filed: Aug. 30, 2011

(65) Prior Publication Data

US 2011/0311993 A1  Dec. 22, 2011

Related U.S. Application Data

(63) Continuation of application No. 12/533,721, filed on Jul. 31, 2009, now Pat. No. 8,012,770.

(51) Int. Cl.
*G01N 33/543* (2006.01)

(52) U.S. Cl. ........ 436/518; 422/401; 422/402; 422/408; 422/420; 422/421; 422/425; 422/426; 422/430; 435/7.21; 435/7.32; 435/7.35; 435/7.37; 435/287.1; 435/287.2; 435/287.7; 435/287.8; 435/287.9; 435/810; 435/970; 436/164; 436/169; 436/170; 436/172; 436/512; 436/514; 436/524; 436/525; 436/530; 436/804; 436/805; 436/807

(58) Field of Classification Search ........................ None
See application file for complete search history.

(56) References Cited

U.S. PATENT DOCUMENTS

| | | |
|---|---|---|
| 3,581,227 A | 5/1971 | Podgorski |
| 4,246,339 A | 1/1981 | Cole et al. |
| 4,254,084 A | 3/1981 | Blum |
| 4,446,232 A | 5/1984 | Liotta |
| 4,727,019 A | 2/1988 | Valkirs et al. |
| 4,797,260 A | 1/1989 | Parker |
| 4,828,801 A | 5/1989 | Lombardy et al. |
| 4,920,046 A | 4/1990 | McFarland et al. |
| 4,994,240 A | 2/1991 | Hayashi |
| 5,003,988 A | 4/1991 | Guirguis |
| 5,133,363 A | 7/1992 | Guirguis |
| 5,137,691 A | 8/1992 | Parker |
| 5,141,850 A | 8/1992 | Cole et al. |
| 5,149,622 A | 9/1992 | Brown et al. |
| 5,155,022 A | 10/1992 | Naqui et al. |
| 5,160,701 A | 11/1992 | Brown, III et al. |
| 5,166,054 A | 11/1992 | Naqui |
| 5,167,924 A | 12/1992 | Clark |
| 5,215,102 A | 6/1993 | Guirguis |

(Continued)

FOREIGN PATENT DOCUMENTS

CA    2024458 A1    3/1991

(Continued)

OTHER PUBLICATIONS

Harlow et al., Antibodies: A Laboratory Manual, 1988, Cold Spring Harbor Laboratory Press, Cold Spring Harbor.

(Continued)

*Primary Examiner* — Chris L Chin
(74) *Attorney, Agent, or Firm* — Pepper Hamilton LLP

(57) ABSTRACT

Devices and methods for the detection of antigens are disclosed. Devices and methods for detecting food-borne pathogens are disclosed.

34 Claims, 10 Drawing Sheets

U.S. PATENT DOCUMENTS

| | | | |
|---|---|---|---|
| 5,358,690 A | 10/1994 | Guirguis | |
| 5,451,504 A | 9/1995 | Fitzpatrick et al. | |
| 5,474,902 A | 12/1995 | Uylen et al. | |
| 5,541,069 A | 7/1996 | Mortensen et al. | |
| 5,559,041 A | 9/1996 | Kang et al. | |
| 5,620,657 A | 4/1997 | Sizto et al. | |
| 5,962,250 A | 10/1999 | Gavin et al. | |
| 6,555,390 B2 | 4/2003 | Chandler | |
| 6,716,641 B1 | 4/2004 | Sundrehagen | |
| 6,766,817 B2 | 7/2004 | Da Silva | |
| 6,770,447 B2 | 8/2004 | Maynard et al. | |
| 7,052,831 B2 | 5/2006 | Fletcher et al. | |
| RE39,664 E | 5/2007 | Gordon et al. | |
| 7,285,255 B2 | 10/2007 | Kadlec et al. | |
| 7,377,904 B2 | 5/2008 | Conway et al. | |
| 7,393,697 B2 | 7/2008 | Charlton | |
| 7,638,093 B2 | 12/2009 | Wang et al. | |
| 7,803,319 B2 | 9/2010 | Yang et al. | |
| 7,815,854 B2 | 10/2010 | Cohen | |
| 7,819,822 B2 | 10/2010 | Calasso et al. | |
| 2002/0115198 A1 | 8/2002 | Nerenberg et al. | |
| 2002/0146346 A1 | 10/2002 | Konecke | |
| 2002/0187561 A1 | 12/2002 | Wong et al. | |
| 2003/0021727 A1 | 1/2003 | Weyker et al. | |
| 2003/0073248 A1 | 4/2003 | Roth et al. | |
| 2003/0207466 A1 | 11/2003 | Po Lee | |
| 2004/0002063 A1 | 1/2004 | Chan et al. | |
| 2004/0018576 A1 | 1/2004 | DeMatteo et al. | |
| 2004/0256230 A1 | 12/2004 | Yager et al. | |
| 2005/0069962 A1 | 3/2005 | Archer et al. | |
| 2005/0163658 A1 | 7/2005 | Wang et al. | |
| 2005/0277202 A1 | 12/2005 | Fleming et al. | |
| 2006/0275851 A1 | 12/2006 | Emmert-Buck et al. | |
| 2007/0009911 A1 | 1/2007 | Joo et al. | |
| 2007/0020768 A1 | 1/2007 | Rundstrom et al. | |
| 2007/0098601 A1 | 5/2007 | Mabuchi et al. | |
| 2007/0202542 A1 | 8/2007 | Babu et al. | |
| 2008/0013949 A1 | 1/2008 | Yoshikane et al. | |
| 2008/0019866 A1 | 1/2008 | Paek et al. | |
| 2008/0199851 A1 | 8/2008 | Egan et al. | |
| 2009/0104715 A1 | 4/2009 | Katada et al. | |
| 2009/0108013 A1 | 4/2009 | Van Der Velde et al. | |
| 2009/0148933 A1 | 6/2009 | Battrell et al. | |
| 2009/0272974 A1 | 11/2009 | Park et al. | |
| 2009/0311668 A1 | 12/2009 | Cheng | |
| 2010/0233028 A1 | 9/2010 | Iwasaki et al. | |
| 2010/0261206 A1 | 10/2010 | Choi et al. | |
| 2010/0322823 A1 | 12/2010 | Surapaneni et al. | |

FOREIGN PATENT DOCUMENTS

| | | |
|---|---|---|
| CA | 2037521 A1 | 11/1991 |
| CA | 2060216 A1 | 9/1992 |
| CN | 101339190 A | 1/2009 |
| CN | 101655494 A | 2/2010 |
| CN | 101726594 A | 6/2010 |
| EP | 0067921 A1 | 12/1982 |
| EP | 0246900 A1 | 11/1987 |
| EP | 0310406 A2 | 4/1989 |
| EP | 0414513 A2 | 2/1991 |
| EP | 0456303 A2 | 11/1991 |
| EP | 0505636 | 9/1992 |
| EP | 0284232 | 9/1998 |
| EP | 1045248 A2 | 10/2000 |
| EP | 1901067 A2 | 3/2008 |
| EP | 2031393 A1 | 3/2009 |
| GB | 1244321 A | 8/1971 |
| KR | 20020097364 A | 12/2002 |
| WO | 8204263 A1 | 12/1982 |
| WO | 88/08534 | 11/1988 |
| WO | 91/12366 | 8/1991 |
| WO | 9813519 A1 | 4/1998 |
| WO | 9836821 A1 | 8/1998 |
| WO | 02059299 A2 | 8/2002 |
| WO | 02077013 A2 | 10/2002 |
| WO | 03016902 A1 | 2/2003 |
| WO | 2005091878 A2 | 10/2005 |
| WO | 2008154237 A2 | 12/2008 |
| WO | 2009034563 A2 | 3/2009 |

OTHER PUBLICATIONS

Fundamental Immunology, 3rd ed. (1993), ed. Paul, Raven Press, New York, N.Y.

Jonio et al., Immunoglobulin Genes, 2nd Ed., 1995, Academic Press, San Diego.

DEVICE FOR DETECTION OF TARGET MOLECULES AND USES THEREOF

CROSS REFERENCE TO RELATED APPLICATIONS

This application is a continuation of U.S. application Ser. No. 12/533,721, filed Jul. 31, 2009, which is hereby incorporated by reference in its entirety.

FIELD OF THE INVENTION

The present invention is directed, in part, to a device and assay for detecting one or more antigens and methods of using the same.

BACKGROUND OF THE INVENTION

Detection of antigens is important for many areas of scientific research, diagnostic use and therapeutic uses. There are several ways in which antigens can be detected. Various methods are described in U.S. Pat. No. 5,160,701, U.S. Pat. No. 5,141,850, PCT Publication WO 91/12336, U.S. Pat. No. 5,451,504, U.S. Pat. No. 5,559,041, European Patent Application No.: 0505636A1, PCT Publication No. WO 88/08534, European Patent Application No. 0284 232A1, U.S. Patent Application Publication No. 20070020768 and U.S. Pat. No. RE39664, each of which is hereby incorporated by reference in its entirety. The methods and devices available prior to the present invention may still require improvements in sensitivity or speed at which results can be obtained. These factors can be important where time is of the essence when attempting to determine the presence or absence of an antigen.

One such area is the area of detecting food borne pathogenic contaminants. Approximately, seventy-six million people in the United States become afflicted with a food borne illness. Of those seventy-six million, approximately, 325,000 will become violently ill, requiring hospitalization, and approximately 5,000 will die. The majority of food-borne illnesses are causes by *Salmonella*, *E. coli*, and *Campylobacter* costing approximately $35 billion dollars.

Current measures at ensuring a safe food supply involve a combination of local, state and federal authorities as well as an elaborate system of inspectors and surveillance networks. Food manufacturers are held to certain United States Department of Agriculture, United States Food and Drug Administration, and the National Marine Fisheries Service regulations that are enforceable by law. The USDA has created a system of health inspectors that are charged with performing daily meat, produce, and other consumable products inspections made or processed in manufacturing and processing facilities. These inspections have been created to involve a detailed statistical analysis to best ensure safety and sterility of food before it reaches the consumer. Moreover, the majority of the meat industry has adopted irradiation techniques to further demonstrate sterility of products. At a lower level, local and municipal health departments work to ensure that local distributors, restaurants, and retailers follow strict guidelines to ensure a safe food supply. However, despite this elaborate network, food-borne infections are still common.

Once an outbreak is strongly suspected, an investigation begins. A search is made for more cases among persons who may have been exposed. The symptoms and time of onset and location of possible cases are determined, and a "case definition" is developed that describes these typical cases. The outbreak is systematically described by time, place, and person. A graph is drawn of the number of people who fell ill on each successive day to show pictorially when it occurred. Calculating the distribution of cases by age and sex shows whom is affected.

Often the causative microbe is not known, so samples of stool or blood must be collected from ill people and sent to the public health laboratory to make a diagnosis. Each collection and sampling can cost upwards of $500 per test and often takes 2-4 days for analysis (CDC "Food-borne Infections").

Prior to the present invention, to identify the food or other source of the outbreak, the investigators first interview a few persons with the most typical cases about exposures they may have had in the few days before they got sick. In this way, certain potential exposures may be excluded while others that are mentioned repeatedly emerge as source possibilities. Combined with other information, such as likely sources for the specific microbe involved, hypotheses are then tested in a formal epidemiologic investigation. The investigators conduct systematic interviews about a list of possible exposures with the ill persons, and with a comparable group of people who are not ill. By comparing how often an exposure is reported by ill people and by well people, investigators can measure the association of the exposure with illness. Using probability statistics, the probability of no association is directly calculated.

As new food-borne problems emerge there is a need for novel devices and methods for detecting food borne pathogens. The present invention provides a device for the detection of antigens, such as antigens from food-borne bacteria, and fulfills the needs of having a device and assay with increased sensitivity and/or speed of detection. The present invention fulfills other needs as well as will be discussed herein.

SUMMARY OF THE INVENTION

In some embodiments, the present invention provides devices for detecting an antigen. In some embodiments, the devices comprise a housing comprising a first housing member and a second housing member, wherein said housing comprises: an inlet opening in the second housing member; a force member attached to the first housing member; a slidable locking member contacting the first housing member and contacting the force member; an antigen detection membrane system comprising in the following order: a conjugate pad; a permeable membrane; a test membrane; and an absorbent member; and a flexible attachment member attached to the locking member and the conjugate pad; wherein at least a portion of each of the conjugate pad, permeable membrane, test membrane, and absorbent member are substantially parallel to each other; wherein the conjugate pad is capable of being compressed against the perimeter of the inlet opening in the second housing member; and wherein the force member contacts the absorbent member and is capable of applying pressure substantially perpendicular to the antigen detection membrane system.

In some embodiments of the devices, the devices further comprise a hydrophobic membrane located between the test membrane and the absorbent member. In some embodiments, the first housing member further comprises a sliding button that protrudes the outer surface of the first housing member, wherein the sliding button is attached to the locking member, wherein movement of the sliding button moves the locking member.

In some embodiments, the conjugate pad comprises a first antigen-specific antibody.

In some embodiments, the antigen recognized by the first antigen-specific antibody is a food-borne pathogen antigen.

In some embodiments, the present invention provides systems comprising a device as described herein and a buffer container or a sample collector.

The present invention also provides methods of detecting an antigen.

DESCRIPTION OF EMBODIMENTS

Figure 1:
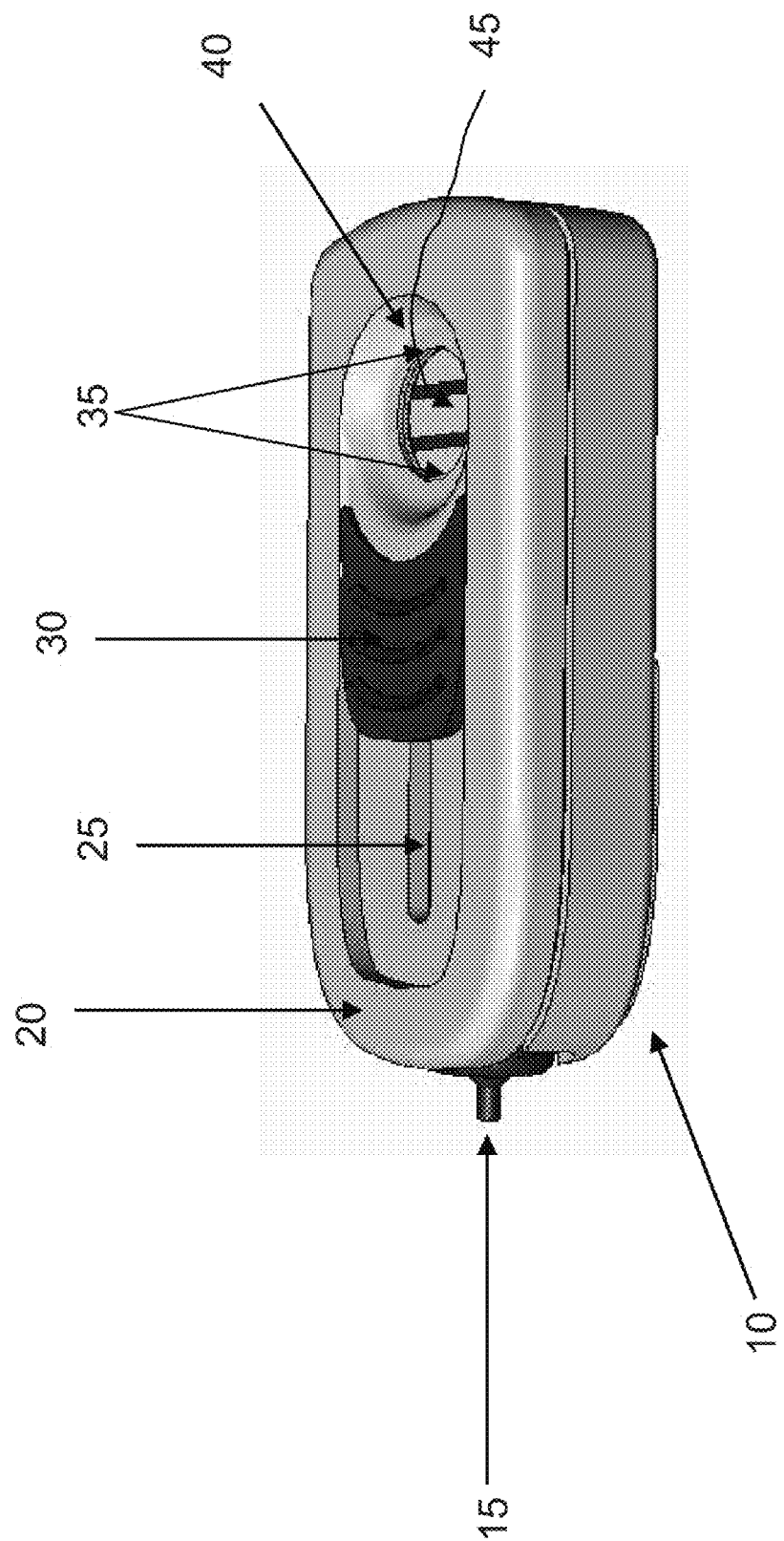
FIG. 1: Depicts a perspective view of a representative device according to some embodiments of the present invention.

As used herein and unless otherwise indicated, the term "about" is intended to mean±5% of the value it modifies. Thus, about 100 means 95 to 105.

The present invention provides devices and methods for detecting antigens or other molecules. In some embodiments, devices in use chromatographic assays. In some embodiments, the assays use specifying binding assays to indicate the presence or absence of an antigen.

The term "capture reagent" refers to a reagent, for example an antibody or antigen binding protein, capable of binding a target molecule or analyte to be detected in a biological sample. A capture reagent may also be, for example, an oligonucleotide or a peptoid.

The term "detecting" or "detection" is used in the broadest sense to include qualitative and/or quantitative measurements of a target analyte.

The terms "attached" or "attachment" can include both direct attachment or indirect attachment. Two components that are directly attached to one another are also in physical contact with each other. Two components that are indirectly attached to one another are attached through an intermediate component. For example, Component A can be indirectly attached to Component B if Component A is directly attached to Component C and Component C is directly attached to Component B. Therefore, in such an example, Component A would be said to be indirectly attached to Component B.

The term "isolated" refers to a molecule that is substantially separated from its natural environment. For instance, an isolated protein is one that is substantially separated from the cell or tissue source from which it is derived.

The term "purified" refers to a molecule that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure.

The terms "specific binding," "specifically binds," and the like, mean that two or more molecules form a complex that is measurable under physiologic or assay conditions and is selective. An antibody or antigen binding protein or other molecule is said to "specifically bind" to a protein, antigen, or epitope if, under appropriately selected conditions, such binding is not substantially inhibited, while at the same time non-specific binding is inhibited. Specific binding is characterized by a high affinity and is selective for the compound, protein, epitope, or antigen. Nonspecific binding usually has a low affinity. Binding in IgG antibodies for example is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody or antigen binding protein carrying the antigen-binding domain will generally not bind other antigens. In some embodiments, the capture reagent has a Kd equal or less than $10^{-9}$M, $10^{-10}$M, or $10^{-11}$M for its binding partner (e.g. antigen). In some embodiments, the capture reagent has a Ka greater than or equal to $10^{9}M^{-1}$ for its binding partner.

Capture reagent can also refer to, for example, antibodies. Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable (V) domain (VL) and a constant (C) domain (CL). Each heavy chain is composed of an N-terminal V domain (VH), three or four C domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

Non-limiting examples of binding fragments encompassed within the term "antigen-specific antibody" used herein include: (i) an Fab fragment, a monovalent fragment consisting of the VL, VH, CL and CH1 domains; (ii) an F(ab')2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue (Gly4Ser)$_3$ peptide, but other linkers are also known in the art. Single chain antibodies are also intended to be encompassed within the terms "antibody or antigen binding protein," or "antigen-binding fragment" of an antibody. The antibody can also be a polyclonal antibody, monoclonal antibody, chimeric antibody, antigen-binding fragment, Fc fragment, single chain antibodies, or any derivatives thereof.

These antibodies are obtained using conventional techniques known to those skilled in the art, and the fragments are screened for utility in the same manner as intact antibodies. Antibody diversity is created by multiple germline genes encoding variable domains and a variety of somatic events. The somatic events include recombination of variable gene segments with diversity (D) and joining (J) gene segments to make a complete VH domain, and the recombination of variable and joining gene segments to make a complete VL domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Antibody or antigen binding protein molecules capable of specifically interacting with the antigens, epitopes, or other molecules described herein may be produced by methods well known to those skilled in the art. For example, monoclonal antibodies can be produced by generation of hybridomas in accordance with known methods. Hybridomas formed in this manner can then be screened using standard methods, such as enzyme-linked immunosorbent assay (ELISA) and Biacore analysis, to identify one or more hybridomas that produce an antibody that specifically interacts with a molecule or compound of interest.

As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature.

The term "capture reagent" also includes chimeric antibodies, such as humanized antibodies, as well as fully humanized antibodies. In some embodiments the capture reagent is a Goat anti-*E. coli* 0157:H7 antibody Cat #: 70-XG13 (Fitzgerald Industries); *E. coli* 0157:H7 mono Cat #: 10-E13A (Fitzgerald Industries); *E. coli* 0157:H7 Cat #: 10C-CR1295M3 (Fitzgerald Industries); *E. coli* 0157:H7 mono Cat #: 10-E12A (Fitzgerald Industries); or Goat anti-mouse IgG Cat #: ABSE-020 (DCN).

In some embodiments, the devices of the present invention comprise a housing comprising a first housing member and a second housing member. In some embodiments, the first and second housing members can be constructed as a single unit. The housing can comprise an inlet opening. The inlet opening allows the introduction of a sample onto the chromatographic assay. In some embodiments, the first housing member comprises the inlet opening. The inlet opening can be of sufficient size to handle an appropriate amount of volume of a solution that is added to the device. In some embodiments, the size of the opening is large enough to handle about 0.1 to 3 ml, about 0.1 to 2.5 ml, about 0.5 to 2.0 ml, about 0.1 to 1.0 ml, about 0.5 to 1.5 ml, 0.5 to 1.0 ml, and 1.0 to 2.0 ml.

In some embodiments, the housing comprises a conjugate pad, a permeable membrane, a test membrane, and/or an absorbent member. In some embodiments, the housing comprises an antigen detection membrane system. In some embodiments, the antigen detection membrane system comprises a conjugate pad, a permeable membrane, a test membrane, and an absorbent member. In some embodiments, the antigen detection membrane system is free of a permeable membrane. In some embodiments, the antigen detection membrane system comprises in the following order: a conjugate pad, a permeable membrane, a test membrane, and an absorbent member.

As used herein, the term "conjugate pad" refers to a membrane or other type of material that can comprise a capture reagent. The conjugate pad can be a cellulose acetate, cellulose nitrate, polyamide, polycarbonate, glass fiber, membrane, polyethersulfone, regenerated cellulose (RC), poly-tetra-fluorethylene, (PTFE), Polyester (e.g. Polyethylene Terephthalate), Polycarbonate (e.g., 4,4-hydroxy-diphenyl-2,2'-propane), Aluminum Oxide, Mixed Cellulose Ester (e.g., mixture of cellulose acetate and cellulose nitrate), Nylon (e.g., Polyamide, Hexamethylene-diamine, and Nylon 66), Polypropylene, PVDF, High Density Polyethylene (HDPE)+ nucleating agent "aluminum dibenzoate" (DBS) (e.g. 80 u 0.024 HDPE DBS (Porex)), and HDPE. Examples of conjugate pads also include, Cyclopore® (Polyethylene terephthalate), Nucleopore® (Polyethylene terephthalate), Membra-Fil® (Cellulose Acetate and Nitrate), Whatman® (Cellulose Acetate and Nitrate), Whatman #12-S (rayon)), Anopore®

(Aluminum Oxide), Anodisc® (Aluminum Oxide), Sartorius (cellulose acetate, e.g. 5 μm), and Whatman Standard 17 (bound glass).

In some embodiments, the conjugate pad or test membrane comprises a capture reagent. In some embodiments, the conjugate pad or test membrane is contacted with the capture reagent and then allowed to dry. The conjugate pad or test membrane can also comprise other compositions to preserve the capture reagent such that it can be stably stored at room temperature or under refrigeration or freezing temperatures. In some embodiments, the conjugate pad or test membrane is soaked with a buffer prior to the capture reagent being applied. In some embodiments, the buffer is a blocking buffer that is used to prevent non-specific binding. In some embodiments, the buffer comprises Borate, BSA, PVP40 and/or Tween-100. In some embodiments, the buffer is 10 mM Borate, 3% BSA, 1% PVP40, and 0.25% Tween-100. In some embodiments the capture reagent is applied to the pad or membrane in a solution comprising trehalose and sucrose. In some embodiments, the capture reagent is applied to the conjugate pad or test membrane in a solution comprising trehalose, sucrose and phosphate and/or BSA. In some embodiments, the capture reagent is applied in a solution that is 5% trehalose, 20% sucrose, 10 mM phosphate, and 1% BSA.

In some embodiments, the pad or membrane (e.g. conjugate pad or test membrane) comprises about 0.5 to about 5.0 μg of a capture reagent, about 1 to about 3 μg of a capture reagent, about 1 to about 2 μg of a capture reagent, about to 2 to about 3 μg of a capture reagent, about 1.5 μg of a capture reagent, 2.5 μg of a capture reagent, or about 2.7 μg of a capture reagent.

In some embodiments, the permeable membrane is attached to or adhered to a test membrane. In some embodiments, the permeable membrane is laminated onto the test membrane. The permeable membrane can be a membrane of any material that allows a sample, such as a fluid sample, to flow through to the test membrane. Examples of test membrane include, but are not limited to, nitrocellulose, cellulose, glass fiber, polyester, polypropylene, nylon, and the like. In some embodiments, the permeable membrane comprises an opening. The opening can be present to allow visualization or detection of the test membrane. In some embodiments, the opening in the permeable membrane is substantially the same size as the inlet opening in the housing. Examples of permeable membranes include, but are not limited to, Protran BA83, Whatman, and the like.

As used herein, the "test membrane" refers to a membrane where detection of a binding partner to a capture reagent occurs. Test membranes include, but are not limited to a nitrocellulose membrane, a nylon membrane, a polyvinylidene fluoride membrane, a polyethersulfone membrane, and the like. The test membrane can be any material that can be used by one of skill in the art to detect the presence of a capture reagent's binding partner (e.g. antigen or epitope). The test membrane can also comprise a capture reagent. In some embodiments, the test membrane is contacted with a capture reagent and the capture reagent is allowed to dry and adhere to the test membrane. Examples of test membranes include, but are not limited to Protran BA83, Whatman, Opitran BA-SA83, and 0.22 μm white plain (Millipore Product No. SA3J036107). The test membrane can comprise a plurality of capture reagents. In some embodiments, the test membrane comprises 1, 2, 3, 4, 5, 6, 7, 8, 9, or 10 capture reagents. In some embodiments, the test membrane comprises a plurality of areas each with a different capture reagent. In some embodiments, the plurality of areas do not completely overlap or coincide with one another. By using a plurality of capture reagents, multiple binding partners (e.g. epitopes or antigens) can be detected.

In some embodiments, the housing also comprises an absorbent member. The absorbent member can also be referred to as a "wick pad" or "wicking pad." The absorbent member absorbs the fluid that flows through the device when the sample is applied to the device and provides for the wicking force that aids in the flow of the sample when it is applied to the device.

The absorbent member can be any material that can facilitate the flow of the sample through the conjugate pad and to the test membrane. Examples of absorbent members include, but are not limited to cellulose, super absorbent polymers, glass fiber pads (e.g. C083 (Millipore)), and the like. In some embodiments, the housing comprises a plurality (e.g. 2 or more) of absorbent members. In some embodiments, the housing comprises 2, 3, 4, or 5 absorbent members. In some embodiments, the absorbent member comprises one or more membranes up to 10 individual membranes, and each membrane may be the same material or a different material.

In some embodiments, the device comprises a force member. The force member can be used to apply pressure or to compress the other components of the antigen detection membrane system against one another. In some embodiments, the force member can comprise a shaft and a head. The force member can have a mushroom type shape where the head is wider than the shaft. In some embodiments, the head is narrower than the shaft. The force member comprising a head and a shaft can be a single unit or can be made up of multiple parts that contact one another to form the force member. For example, the head could be one unit that can be separated from the shaft. Upon assembly the head and shaft are contacted with one another to make the force member. In another example, the head and shaft are one cohesive unit and are manufactured together and not as separate parts that are later assembled to form the force member. The force member allows the device to work with vertical flow as opposed to relying upon lateral flow.

The devices described herein can be used in assays to detect the presence of a capture reagent's binding partner. For example, an antigen can be detected by an antibody using the devices of the present invention. The devices of the present invention employ vertical flow. "Vertical flow" refers to the direction that the sample flows across the different membranes and members present in the device. Vertical flow refers to a sample flowing through the membrane (e.g. top to bottom) as opposed to lateral flow, which refers to a sample flowing across (e.g. side to side) a membrane, pad or absorbent member. In a lateral flow device the membranes and pads sit horizontally adjacent to one another substantially on the same plane. In a vertical flow device each membrane or pad is substantially parallel or completely parallel to each other and occupy substantially different spatial planes in the device. The membranes and pads may occupy similar planes when they are compressed or put under pressure. In some embodiments, at least a portion of each membrane or pad is layered on top of each other. In some embodiments, at least a portion of each layer of membrane or pad is substantially parallel to each other. In some embodiments, at least a portion of each layer is in a different spatial plane than each other layer.

To allow vertical flow to occur efficiently, in some embodiments, the conjugate pad, permeable membrane, test membrane and the absorbent member are substantially parallel to each other. In some embodiments, the conjugate pad, permeable membrane, test membrane and the absorbent member are present in different spatial planes. In some embodiments, the housing also comprises a hydrophobic membrane that can slow or stop the vertical flow of the sample. The hydrophobic membrane can be in contact with the test membrane, which would allow the sample to dwell or rest upon the test membrane. The dwell can allow for increased sensitivity and detection. The vertical flow is modulated by the pressure that is applied to the membranes. In some embodiments, the pressure is applied perpendicular to the test membrane and/or the conjugate pad. The pressure can be applied so that the conjugate pad is compressed against the housing. The compression against the housing can be such that the conjugate is in direct contact with the housing, O-ring, or collar, or through an intermediate so that the conjugate pad and the test membrane are compressed against one another.

The force member can apply pressure that is substantially perpendicular to the test membrane. The pressure facilitates the vertical flow. The pressure allows each layer of the membrane stack to be in contact with another layer. The pressure can also be relieved to stop the flow so that the test sample can dwell or rest upon the test membrane, which can allow for greater sensitivity. The pressure can then be reapplied to allow the vertical flow to continue by allowing the sample to flow into the absorbent member(s). The force member can apply pressure such that the conjugate pad contacts a portion of the housing. In some embodiments, the conjugate pad contacts the housing when it is not under the pressure being exerted by the force member but upon the force member exerting pressure the conjugate pad is compressed against a portion of the housing.

In some embodiments, the conjugate pad contacts the perimeter of the inlet opening. The inlet opening can also comprise a collar or other similar feature, such as an O-ring. In some embodiments, the conjugate pad contacts the perimeter of a collar and/or an O-ring. In some embodiments, the conjugate pad is capable of being compressed against the perimeter of the inlet opening, which can include, in some embodiments, a collar and/or an O-ring.

"Capable of being compressed against the perimeter of the inlet opening" refers to a membrane or pad (e.g. conjugate pad) being compressed either directly in contact with the perimeter of the inlet opening or being compressed against another layer or material (e.g. membrane) that is in contact with the perimeter of the inlet opening.

In some embodiments, the conjugate pad is not in direct physical contact with the housing but is in fluid contact with the housing. "Fluid Contact" means that if a sample is applied to the device through the inlet opening or other opening the fluid will contact the conjugate pad. In some embodiments, the conjugate pad can be separated from the housing by another membrane, such as a permeable membrane, where the other membrane is in direct physical contact with the housing or in direct physical contact with the collar or O-ring. When the sample is applied to the device the fluid can contact the other membrane first and then contact the conjugate pad. This is just one example of the conjugate pad being in fluid contact with the housing. There are numerous other embodiments where the conjugate pad is not in direct physical contact with the housing, the collar, or the O-ring, but is in fluid contact with the housing.

The force member can apply any pressure that is sufficient to facilitate vertical flow across the different membrane layers. In some embodiments, the layers of the device (e.g. conjugate pad, permeable membrane, test membrane, and absorbent member) are compressed under a force chosen from about 5 lbf to 100 lbf, about 5 lbf to 50 lbf, about 10 lbf to 40 lbf, about 15 lbf to 40 lbf, about 15 lbf to 25 lbf, or about 30 lbf to 40 lbf. The force can also compress a hydrophobic or impermeable membrane as well if one is present in the device.

In some embodiments, the force member contacts a first surface of an absorbent member. In some embodiments, a conjugate pad contacts a test membrane. In some embodiments, a first surface of a test membrane contacts a permeable membrane. In some embodiments, a second surface of the test membrane contacts a second surface of the absorbent pad. In some embodiments, the device comprises a hydrophobic membrane, and, for example, the hydrophobic membrane contact a second surface of the test membrane. In some embodiments, the hydrophobic membrane contact a first surface of the absorbent pad.

In some embodiments, a first surface of the conjugate pad contacts the housing and a second surface of the conjugate pad contacts a first surface of the permeable membrane, wherein the second surface of the permeable membrane contacts a first surface of the test membrane, wherein a second surface of the test membrane contacts a first surface of the absorbent pad, wherein a second surface of the absorbent pad contacts the force member. In some embodiments, the first surface of the conjugate pad contacts a perimeter of the inlet opening of said housing. In some embodiments, the first surface of the conjugate pad contacts a perimeter of a collar or an O-ring.

The device can also comprise an attachment member. In some embodiments, the attachment member is flexible or made from a flexible material. The flexible material can be, for example, an elastic or elastomer material. An attachment member can be, for example, attached to a conjugate pad and/or a hydrophobic membrane. The attachment member can also be attached to any membrane or member of the device. Examples of attachment members include, but are not limited to, elastomer band, rubber band, spring, and the like. In some embodiments, the attachment member can be made of a shape memory material. The attachment member makes it possible to create a delay between moving the locking member and moving the conjugate pad or any other type of membrane or pad that the attachment member is attached to. The movement of the pad or membrane does not happen at the same time as the sliding button or locking member is moved. Not being bound to any particular theory, as the sliding button or locking member is moved energy is accumulated in the attachment member and this energy is used to pull on a pad or membrane that it is attached to the attachment member after the pressure has been released. In some embodiments, the locking member is moved away from the force member (i.e., the force member no longer contacts the locking member) before the conjugate pad is moved or removed. The conjugate pad, in some embodiments, is moved once the compression or pressure being exerted by the force member is completely removed.

The attachment member can also be attached to either a sliding button or locking member. The attachment member can be attached through any means such as, adhesives, staples, tying, and the like to the other components. In some embodiments, the membrane or pad has notches in the membrane or pad that allow the attachment member to attach to the membrane or pad. A non-limiting example can be seen in FIG. 9.

In some embodiments, the housing comprises a locking member. The locking member can be a slidable locking member that can move within the device. The locking member can be used to lock the force member in a position such that the force created by the force member upon the different layers is maintained. The locking member is, for example, locking the force member in place so that the pressure cannot be relieved unless the locking member is moved to allow the force member to change positions (i.e. lowered). The locking member, can for example, fit under the head of the force member, which would keep the force member in the raised position. The locking member can also be situated so that it keeps the force member in a particular position (e.g. raised or lowered). The locking member can be made of any material including, but not limited to, plastic and the like. The locking member can, for example, contact the force member either directly or indirectly through another component that prevents the force member from releasing the pressure. In some embodiments, the locking member contacts the force member to compress the conjugate pad.

The locking member can also contact the attachment member such that movement of the locking member will move the attachment member, any other membrane (e.g. conjugate pad, hydrophobic membrane, test membrane, or absorbent member) or other component that is attached to the attachment member. For example, if the locking member is moved to relieve the pressure of the force member thereby allowing the force member to change positions (e.g. from raised to a lower position), the movement of the locking member will also deform/accumulate energy into the attachment member so it can move the membrane or pad once the pressure has been sufficiently reduced. When the conjugate pad is attached to the attachment member and the locking member is moved this will also move the conjugate pad once the pressure has been sufficiently reduced. In some embodiments, the pressure is completely removed. The conjugate pad can be, for example, moved such that it is removed from the device. In some embodiments, the conjugate pad is moved to reveal the test membrane through the inlet opening. The amount of the test membrane that is revealed will depend upon the type of detection that is used. For a visual detection more of the test membrane may need to be revealed in the inlet opening. For a non-visual, e.g. fluorescent, infrared, radioactive or chemiluminescent detection, less of the test membrane may need to be revealed. In some embodiments, the conjugate pad is moved so that it no longer can be seen or detected through the inlet opening. In some embodiments, the movement of the conjugate pad can create another opening other than the inlet opening to visualize or detect the test membrane.

In some embodiments, the attachment member is also attached to the impermeable or hydrophobic membrane. When the attachment member is moved the movement will also move or remove the impermeable or hydrophobic membrane. As discussed herein, the presence of the impermeable or hydrophobic membrane can allow the test sample to dwell or rest upon the test membrane by slowing or stopping the vertical flow. When the impermeable or hydrophobic membrane is moved or removed, either by its attachment to the attachment member or through other means, the vertical flow is no longer impeded or inhibited.

In some embodiments, the housing comprises a sliding button. A sliding button can also be referred to as a sliding member. The sliding button can cross the inner and outer surfaces of the housing. In some embodiments, the sliding button or sliding member protrudes to an outer surface of the housing. In some embodiments, the sliding button is attached either directly or indirectly to the locking member. When the sliding button is attached (directly or indirectly) to the locking member the movement of the sliding button also moves the locking member. The attachment member in some embodiments can be attached to the sliding button. In some embodiments, the attachment member is attached to both the sliding button and the locking member. The sliding button and the locking member can also be constructed as a single unit.

In some embodiments, the inlet opening comprise an opening chosen from a range of about 0.2-20 $cm^2$. In some embodiments, the inlet opening is about 1 to about 2 cm in diameter. In some embodiments, the inlet opening is about 1 or about 1.5 cm in diameter. In some embodiments, the inlet opening is about 1, about 2, about 3, about 4, or about 5 cm in diameter.

As discussed herein, the conjugate pad can comprise an antigen specific capture reagent. In some embodiments, the conjugate pad comprises a plurality of antigen specific capture reagents. In some embodiments, the conjugate pad comprises 1, 2, 3, 4, or 5 antigen specific capture reagents. The antigen can be any molecule that can be specifically recognized by a capture reagent. Examples of antigens include a polynucleotide molecule (e.g. DNA, RNA, siRNA, antisense oligonucleotide) a peptide, a protein, a saccharide, a polysaccharide, a carbohydrate, and the like. The antigen can also refer to different epitopes present on the same protein or polypeptide.

The capture reagent can also be, for example, protein A, protein G, and the like.

In some embodiments, the protein is a pathogen protein. A pathogen protein refers to a protein that is from a pathogen. Examples of pathogens include, but are not limited to, viruses, prokaryote and pathogenic eukaryotic organisms such as unicellular pathogenic organisms and multicellular parasites. Pathogens also can include protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins.

Bacterial pathogens include, but are not limited to, such as bacterial pathogenic gram-positive cocci, which include but are not limited to: pneumococcal; staphylococcal; and streptococcal. Pathogenic gram-negative cocci include: meningococcal; and gonococcal. Pathogenic enteric gram-negative bacilli include: enterobacteriaceae; pseudomonas, acinetobacteria and *eikenella*; melioidosis; *salmonella*; shigellosis; *hemophilus*; chancroid; brucellosis; tularemia; *yersinia* (pasteurella); *streptobacillus moniliformis* and spirilum; *listeria monocytogenes; erysipelothrix rhusiopathiae*; diphtheria; cholera; anthrax; donovanosis (granuloma inguinale); and bartonellosis. Pathogenic anaerobic bacteria include; tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and *chromomycosis*; and dermatophytosis. Rickettsial infections include rickettsial and rickettsioses. Examples of mycoplasma and chlamydial infections include: *mycoplasma pneumoniae*; lymphogranuloma venereum; psittacosis; and perinatal chlamydial infections. Pathogenic protozoans and helminths and infections eukaryotes thereby include: amebiasis; malaria; leishmaniasis; trypanosomiasis; toxoplasmosis; *pneumocystis carinii*; babesiosis; giardiasis; trichinosis; filariasis; schistosomiasis; nematodes; trematodes or flukes; and cestode (tapeworm) infections. Bacteria also include *E. coli*, an *Campylobacter*, and a *Salmonella*.

In some embodiments, *E. Coli* is *E. coli* 0157.

Examples of viruses include, but are not limited to, HIV, Hepatitis A, B, and C, FIV, lentiviruses, pestiviruses, West Nile Virus, measles, smallpox, cowpox, ebola, coronavirus, and the like. Other pathogens are also disclosed in U.S. Patent Application Publication No. 20080139494, which are incorporated by reference.

In some embodiments, the pathogen is a food borne pathogen. The antigen can be present on a food borne pathogen. Food borne pathogens are pathogens (e.g. viral or bacterial) that cause illness after eating contaminated food. The food itself does not directly cause the illness, but it is rather the consumption of the food borne pathogen that is present on the food that causes the illness. In some embodiments, the food borne pathogen is *E. coli, Campylobacter*, or *Salmonella*. In some embodiments, the antigen is an antigen chosen from a food borne pathogen antigen. For example, the food borne pathogen antigen can be, but is not limited to, chosen from an *E. coli* antigen, a *Campylobacter* antigen, or a *Salmonella* antigen. In some embodiments, the antigen is the species specific O-Antigen. In some embodiments, the O-antigen is the *E. coli* and/or the *Salmonella* O-antigen and can be used for *E. coli* and *Salmonella* detection. In some embodiments, the antigen is a flagellin antigen. In some embodiments, the antigen is the *Campylobacter flagellin* antigen.

In some embodiments, the capture reagent comprises a detection reagent. The detection reagent can be any reagent that can be used to detect the presence of the capture reagent binding to its specific binding partner. The capture reagent can comprise a detection reagent directly or the capture reagent can comprise a particle that comprises the detection reagent. In some embodiments, the capture reagent and/or particle comprises a color, colloidal gold, radioactive tag, fluorescent tag, or a chemiluminescent substrate. The particle can be, for example, a viral particle, a latex particle, a lipid particle, or a fluorescent particle. In some embodiments, the colloidal gold has a diameter size of: about 20 nm, about 30 nm, or about 40 nm or in the range of about 20-30 nm, about 20-40 nm, about 30-40 nm, or about 35-40 nm.

In some embodiments, the test membrane also comprises one or more capture reagents.

The capture reagents of the present invention can also include an anti-antibody, i.e. an antibody that recognizes another antibody but is not specific to an antigen, such as, but not limited to, anti-IgG, anti-IgM, or ant-IgE antibody. Where the test membrane comprises an anti-antibody, such as anti-IgG, anti-IgM, or anti-IgE antibody, this non-specific antibody can be used as a positive control to detect whether the conjugate has been released from the conjugate pad. When the sample is applied to the device it allows a first capture reagent to be released from the conjugate pad. As the capture reagent is released and flows through the device, either attached to the antigen or not, it can contact the anti-antibody, such as anti-IgG or anti-IgM antibody, which can then be detected. This detection can be used to show that the device is working properly.

In some embodiments, the test membrane comprises a second antigen specific capture reagent. In some embodiments, the test membrane comprises a first area comprising a first capture reagent comprising an anti-IgG capture reagent; and a second area comprising a second antigen specific capture reagent, wherein the first and second areas do not completely overlap or coincide with one another. This non-limiting embodiment can be used to demonstrate the device is working properly and be used to detect the presence of the antigen of interest.

In some embodiments, the conjugate pad comprises a first antigen specific capture reagent and the test membrane comprises a second antigen specific capture reagent, wherein the first and second antigen specific capture reagents bind to non-competitive epitopes present on the antigen. The device can, for example, employ a sandwich type assay that occurs in two steps. The first step is the binding of the antigen to the capture reagent present in the conjugate pad. After binding to the first antigen specific capture reagent the antigen can flow through to or make contact with the test membrane where a second antigen specific capture reagent is present. Upon interaction with the test membrane if the test antigen can bind to the second antigen-specific capture reagent it will be able to be detected either through visualization or through the use of another detection device such as, but not limited to, a fluorescent reader. The test membrane and the conjugate pad can comprise additional antigen-specific capture reagents that recognize different antigens or different epitopes. In some embodiments, the test membrane or the conjugate pad comprises 1, 2, 3, 4, 5, 6, 7, 8, 9, 10 antigen-specific capture reagents. In some embodiments, the test membrane or the conjugate pad comprises a plurality of antigen-specific capture reagents. In some embodiments, each antigen-specific capture reagent recognizes a different antigen or a different epitope on the same antigen.

"Different antigens" can also refer to the same protein but a protein that is from different strains of the same organism. Different antigens can also refer to antigens from different organisms. For example, there are any many strains of *E. coli*. Not all strains of *E. coli* cause a food-borne illness. The present invention can be used, for example, to detect an antigen from a pathogenic *E. coli* strain as opposed to detecting an antigen from a non-pathogenic *E. coli* strain. In some embodiments, the conjugate pad and/or test membrane comprises a first and a second antigen-specific capture reagents, wherein the first and said second capture reagents recognize different antigens. In some embodiments, the test membrane and/or conjugate pad comprises a plurality of areas comprising a plurality of antigen-specific capture reagents, wherein the plurality of antigen-specific capture reagents recognize different antigens. In some embodiments, the plurality of areas do not completely overlap or coincide with one another. In some embodiments, the plurality of antigens are each independently chosen from an *E. coli* antigen, an *Campylobacter* antigen, and a *Salmonella* antigen. In some embodiments of the present invention, the plurality of antigens is 2, 3, 4, 5, 6, 7, 8, 9, 10, or more than 10 antigens.

The devices may be housed singly, in pairs, or in multiple configurations. The housing can be watertight to prevent leakage and can be manufactured from a variety of inert materials, such as polymer materials. The inlet opening, in some embodiments, can be of sufficient volume to contain any required amount of sample or reagents to be used with the invention.

Because the membranes or pads of the device is preferably chemically inert, it may have to be activated at any reaction site where it is desired to immobilize a specific binding reagent against solvent transport. Various methods may be required to render the reagent immobilized according to the particular chemical nature of the reagent. Generally, when the media is nitrocellulose or a mixed nitrocellulose ester, no special chemical linkage is required for the immobilization of reagents. Various techniques may be used for other materials and reagents which include functionalization with materials such as carbonyldiimidazole, glutaraldehyde or succinic acid, or treatment with materials such as cyanogen bromide. Other suitable reactions include treatment with Schiff bases and borohydride for reduction of aldehyde, carbonyl and amino groups. DNA, RNA and certain antigens may be immobilized against solvent transport by baking onto the chromatographic material. Baking may be carried out at temperatures ranging from about 60° C. to about 120° C. for times varying from about five minutes to about 12 hours, and in some embodiments, at about 80° C. for about two hours.

The present invention also provides systems comprising the devices described herein and a buffer container. The buffer container can be any buffer that the sample that is being tested can be mixed with and then applied to the device. For example, the sample can be taken from a source and the sample can be mixed with the buffer. The buffer can be a lysis buffer that will lyse the cells or a buffer that maintains the pH of the sample so that the analysis can be done properly. The buffer container can be any shape and can be included outside or inside the housing of the device.

In some embodiments, the present invention provides a system that comprises a sample collector. The sample collector can be any material that can take a sample from a source and allow the sample to be tested. For example, the sample collector can be a swab, such as a cotton-swab. In some embodiments, the sample collector is an innoculator. In some embodiments, the housing comprises the sample collector and a portion of the sample collector is in the inside of the housing. In some embodiments, the sample collector is partially outside and partially inside the housing. In some embodiments, the sample collector is completely outside the housing.

The present invention also provides for kits comprising the devices described herein. The kit can include a device as described herein, a sample collector, a buffer container, an instruction manual, a positive control, a negative control, or any combination thereof. With respect to the kit, a positive control is a sample that is known to contain the antigen that can be detected with the device present in the kit. In contrast the negative control, would not contain an antigen that can be detected by the kit. The negative control when used in conjunction with the anti-antibody would be able to demonstrate that the device is working properly.

Buffers can also be included in the present invention. Examples of buffers include, but are not limited to, 1×PBS (10 mM Phosphate, 137 mM Sodium Chloride, 2.7 mM Potassium Chloride), a wash buffer (e.g. 10 mM Sodium Phosphate, 150 mM NaCl, 0.5% Tween-20, 0.05% Sodium Azide), a membrane buffer (e.g. 10 mM Sodium Phosphate, 0.1% Sucrose, 0.1% BSA, 0.2%, PVP-40 pH 7.21, filtered with 0.2 µm filter.), Polyclonal Conjugate Block Buffer (e.g. 50 mM Borate, 10% BSA, pH 8.93); Polyclonal Conjugate Diluent (e.g. 50 mM Borate, 1% BSA, pH 9.09), or Blocking Buffers (e.g. 10 mM Sodium Phosphate, 0.1% Sucrose, 0.025% Silwet pH 7.42; 10 mM Sodium Phosphate, 1% Sucrose, 1% Trehalose, 0.01% BSA, 0.025% Tween-20; 0.05% Sodium Azide, 0.025% Silwet pH 7.4; 10 mM Sodium Phosphate, 0.1% Sucrose, 0.1% BSA, 0.2% PVP-40 pH 7.21). The buffer can also be, but is not limited to, a blocking buffer (e.g. 10% BSA in deionized water, pH 7.4 or 1% BSA in deionized water, pH 7.4); 10 mM Borate, 3% BSA, 1% PVP40, and 0.25% Tween-100; and the like.

The conjugate pad and the test membrane can be contacted with any of the buffers described herein either in the presence or absence of a capture reagent and, in some embodiments, allowed to dry.

Examples of buffers that are lysis buffers include, for example, but are not limited to, 2% Tween (v/v) and 0.1% Triton(v/v); 2% Tween(v/v) and 0.1% SDS(w/v); 2% Tween (v/v) and 0.1% BSA(w/v); 2% Tween(v/v) and 1% BSA(w/v), 0.1% SDS(w/v), 1% BSA(w/v), or any combination thereof. The lysis buffers can also be, for example, 5% Tween/PBS; 2% Tween/PBS+0.1% SDS; 2% Tween/PBS+1% BSA. Other examples of lysis buffers include, but are not limited to, 5% Tween-80(v/v); 5% Triton X-100(v/v); 5% NP40(v/v); 2% Tween-80(v/v); 2% Triton X-100(v/v); 2% NP40(v/v); 1% Tween-80(v/v); 1% Triton X-100(v/v); and 1% NP40(v/v). The detergents and other components of the buffers can be made with any suitable buffer suitable for proteins, and includes, but is not limited to, water and phosphate buffered saline. The lysis buffers can be used to prepare the samples prior to the samples making contact with the devices described herein. In some embodiments, a lysis buffer is not used. A lysis buffer is not used on a sample when a surface protein or surface antigen is desired to be detected. Accordingly, in some embodiments, the sample is not subject to lysis or conditions that would cause a cell to be lysed.

The present invention also provides for methods of detecting an antigen comprising contacting a sample with a device as described herein, wherein the sample contacts the conjugate pad and the test membrane, wherein a positive reaction with the test membrane indicates the presence of the antigen, wherein the conjugate pad comprises a first antigen-specific capture reagent and the test membrane comprises a second antigen-specific capture reagent. A positive reaction is indicated by the capture reagent present in the test membrane binding to an antigen in the test sample. The capture reagent in the test membrane is applied to the test membrane so that it will indicate a positive reaction when it binds to its specific antigen. The specific capture reagent can be applied in any manner such that when it is detected it can form a line, a circle, a plus sign, a broken line, an "X" or any other pattern. In some embodiments, the control line indicating that the device is working properly will cross the antigen specific line and when the antigen specific capture reagent binds to the antigen the detectable label will form a plus sign.

In some embodiments, a sample contacts the device, which is then followed by a buffer being applied to the device after the sample has contacted the device. For example, a sample comprising an antigen can be contacted with the conjugate pad such that the sample is transferred to the conjugate pad. Following the contact with the conjugate pad a separate solution can be applied to the device to facilitate or initiate the vertical flow through the devices described herein.

In some embodiments as described herein the capture reagent is an antibody. In some embodiments, the sample that is tested is a solution but can also be a mixture of solution or buffer and solid material that can be applied to the device. The solution will then solubilize the antigen and allow the conjugate pad's capture reagent to come into contact with the antigens present in the sample. In some embodiments, the sample comprises a cell lysate. In some embodiments, the cell lysate has been clarified by centrifugation or other means to remove non-soluble materials.

In some embodiments, the methods comprise contacting a test sample with a sample collector and contacting the sample collector with the device. In some embodiments, the methods comprise contacting the sample collector with a solution or buffer, wherein the solution or buffer is applied to the device. In some embodiments, the samples are contacted with the conjugate pad prior to the sample coming into contact with the test membrane. In some embodiments, the sample is contacted with the conjugate pad and the test membrane simultaneously.

In some embodiments, the method comprises moving the conjugate pad of the devices described herein, wherein the movement of the devices exposes the test membrane for detection. In some embodiments, the locking member moves the conjugate pad. In some embodiments, the conjugate pad is attached to the locking member and/or the sliding button member. The antigen that the method can be used to detect can be any antigen. The antigen can be those that are discussed herein or any other antigen that can be detected using the methods and devices described herein. In some embodiments, the method comprises applying the sample to the device and allowing the sample to flow through the device via vertical flow.

In some embodiments the detection or indication of the presence or absence of an antigen occurs in less than 60 seconds. In some embodiments, the detection or indication of the presence or absence of an antigen occurs in about 30 to about 60 seconds. In some embodiments, the detection or indication of the presence or absence of an antigen occurs in less than 2 minutes. In some embodiments, the detection or indication of the presence or absence of an antigen occurs in about 30 seconds.

Referring to the drawings, in some embodiments, FIGS. 1 through 10, depicts representative devices, components of a device, and various views of a device. FIG. 1 depicts a device comprising a first housing member (10), a buffer container (15), a second housing member (20), a groove for the sliding button (25), a sliding button (30), an inlet opening (35), a collar (40), and a test membrane (45). FIG. 1 depicts a test membrane (45) comprising two capture reagents. The first (10) and second (20) housing members can also be referred to as the lower and upper housing members, respectively. In FIG. 1, the sample would be applied through the inlet opening (35) and can be allowed to vertically flow through to the test membrane (45). In FIG. 1, the groove (25) allows the sliding button to move, which when attached to the locking member moves the locking member and can, in some embodiments, move the conjugate pad and change the position of the force member.

Figure 2:
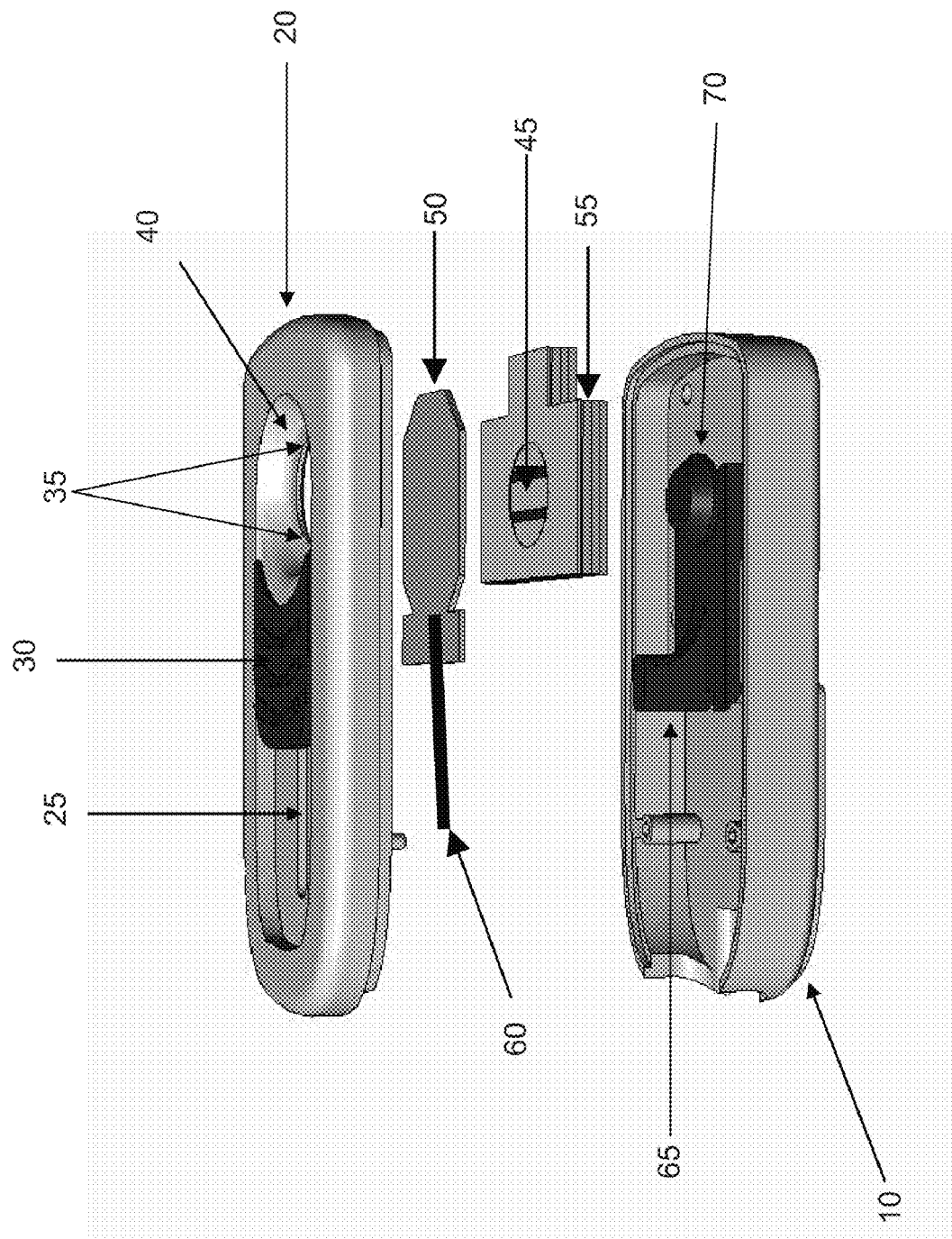
FIG. 2: Depicts some components of a representative device according to some embodiments of the present invention.

FIG. 2 depicts a device comprising a first housing member (10), a second housing member (20), a groove for the sliding button (25), a sliding button (30), an inlet opening (35), a collar (40), a test membrane (45), a conjugate pad (50), a plurality of absorbent members (e.g. pads) (55), an attachment member (60), a locking member (65), and a force member (70). FIG. 2 depicts the conjugate pad (50), test membrane (45) and absorbent pad (55) arranged substantially parallel to one another. The force member (70) when in contact with the absorbent member would be applying pressure that is substantially perpendicular to the conjugate pad. As can be seen in FIG. 2, a sample that is contacted with the device through the inlet opening (35) would flow vertically through the conjugate pad (50) to the test membrane (45). Not explicitly shown in FIG. 2, but in some embodiments, a the permeable membrane is also substantially parallel to the conjugate pad (50) and to the test membrane (45), with a first surface of the permeable membrane contacting a surface of the conjugate pad (50) a second surface of the permeable membrane contacting a surface of the test membrane (45).

Figure 3:
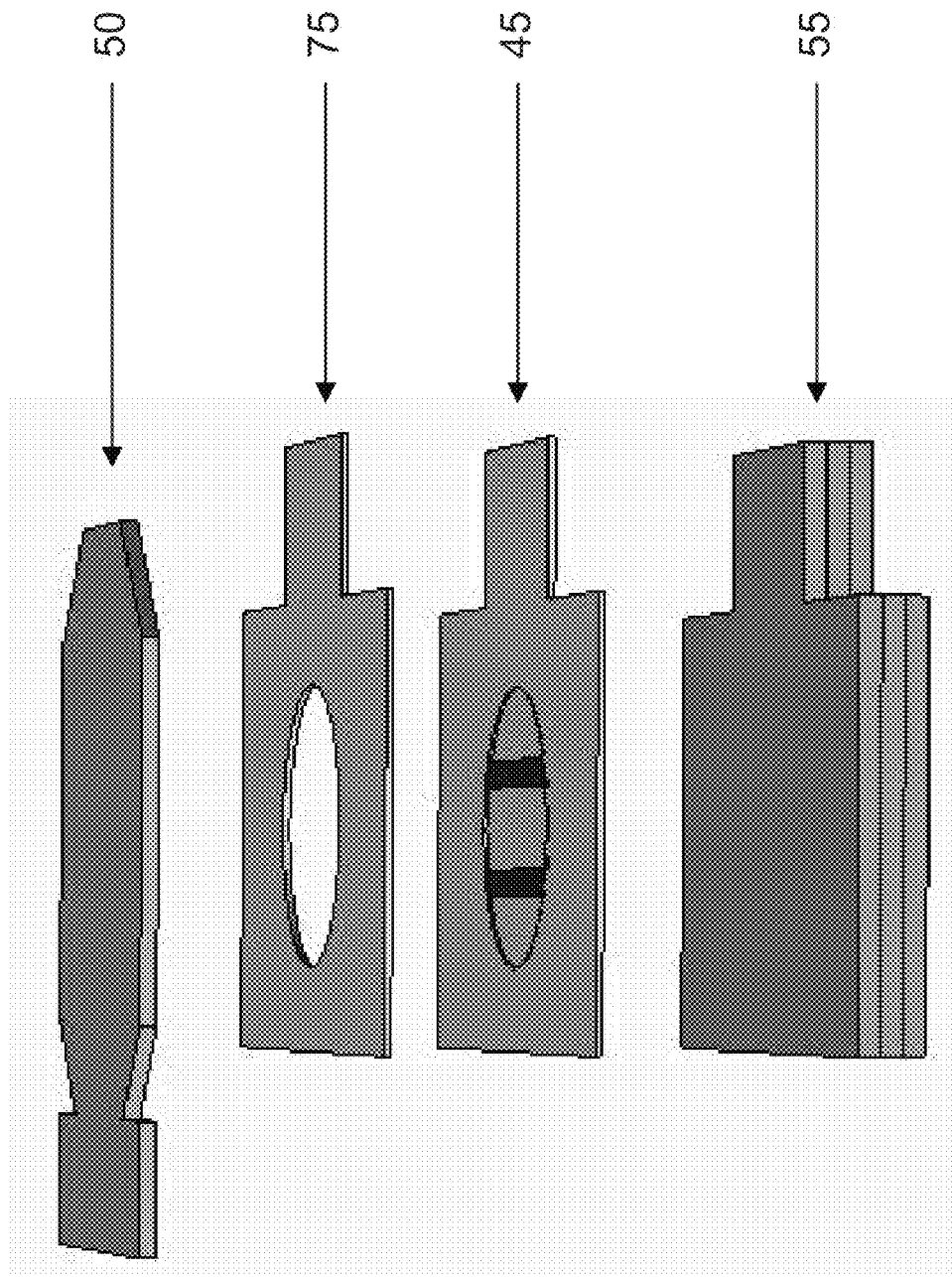
FIG. 3: Depicts some components of a representative device according to some embodiments of the present invention.

FIG. 3 depicts a conjugate pad (45), a permeable membrane (75), a test membrane (45), and a plurality of absorbent members (55). FIG. 3 depicts the components being substantially parallel with one another. FIG. 3 depicts the permeable membrane (75) comprising an opening. This opening can be used to allow visualization and detection of the test membrane's results.

Figure 4:
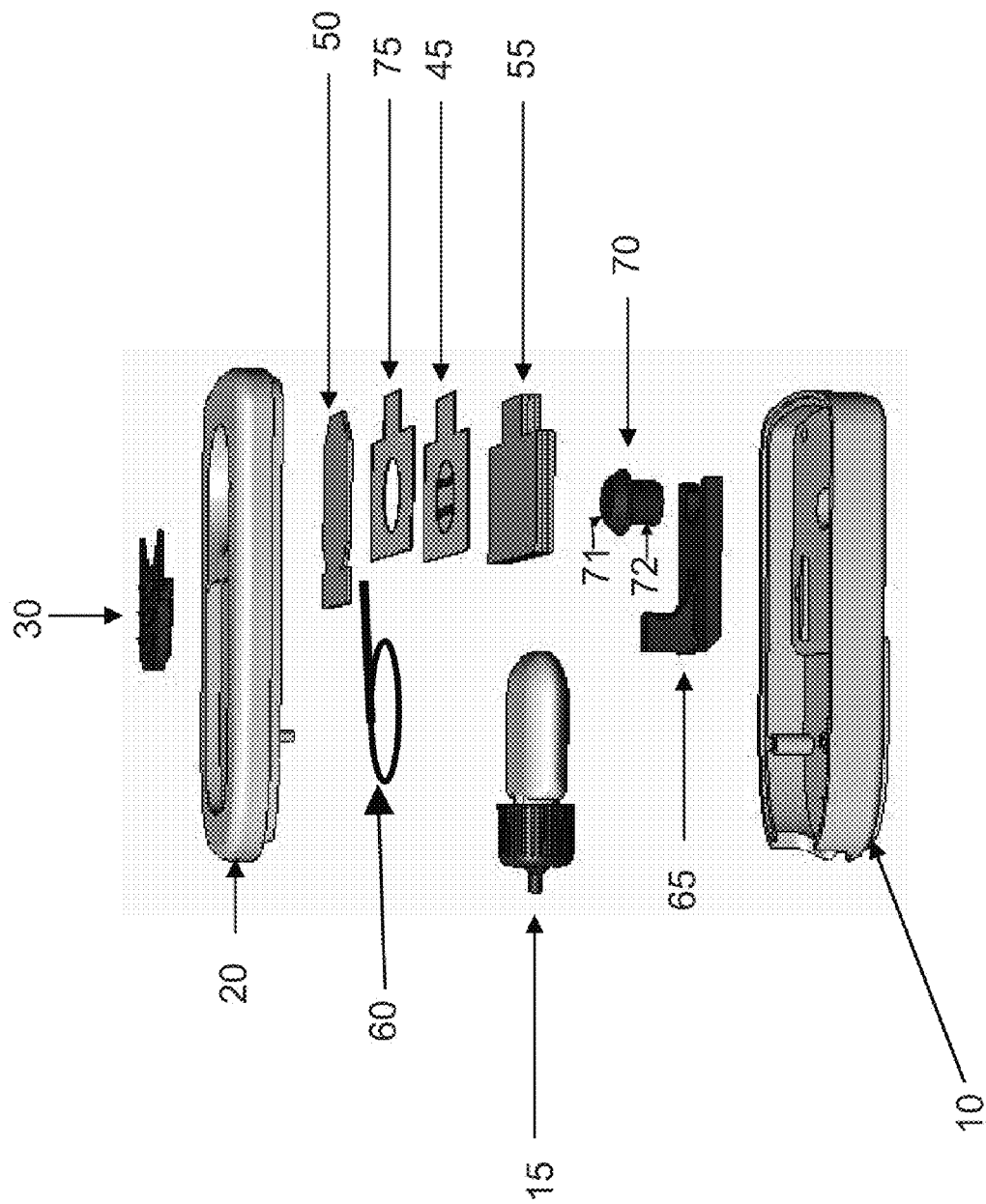
FIG. 4: Depicts some components of a representative device according to some embodiments of the present invention.

FIG. 4 depicts a device comprising a first housing member (10), a buffer container (15), a second housing member (20), a sliding button (30), a test membrane (45), a conjugate pad (50), a permeable membrane (75), a plurality of absorbent members (e.g. pads) (55), an attachment member (60), a locking member (65), and a force member (70). FIG. 4 also depicts the force member (70) comprising a shaft (72) and a head (71) where the head (71) is wider than the shaft (72).

Figure 5:
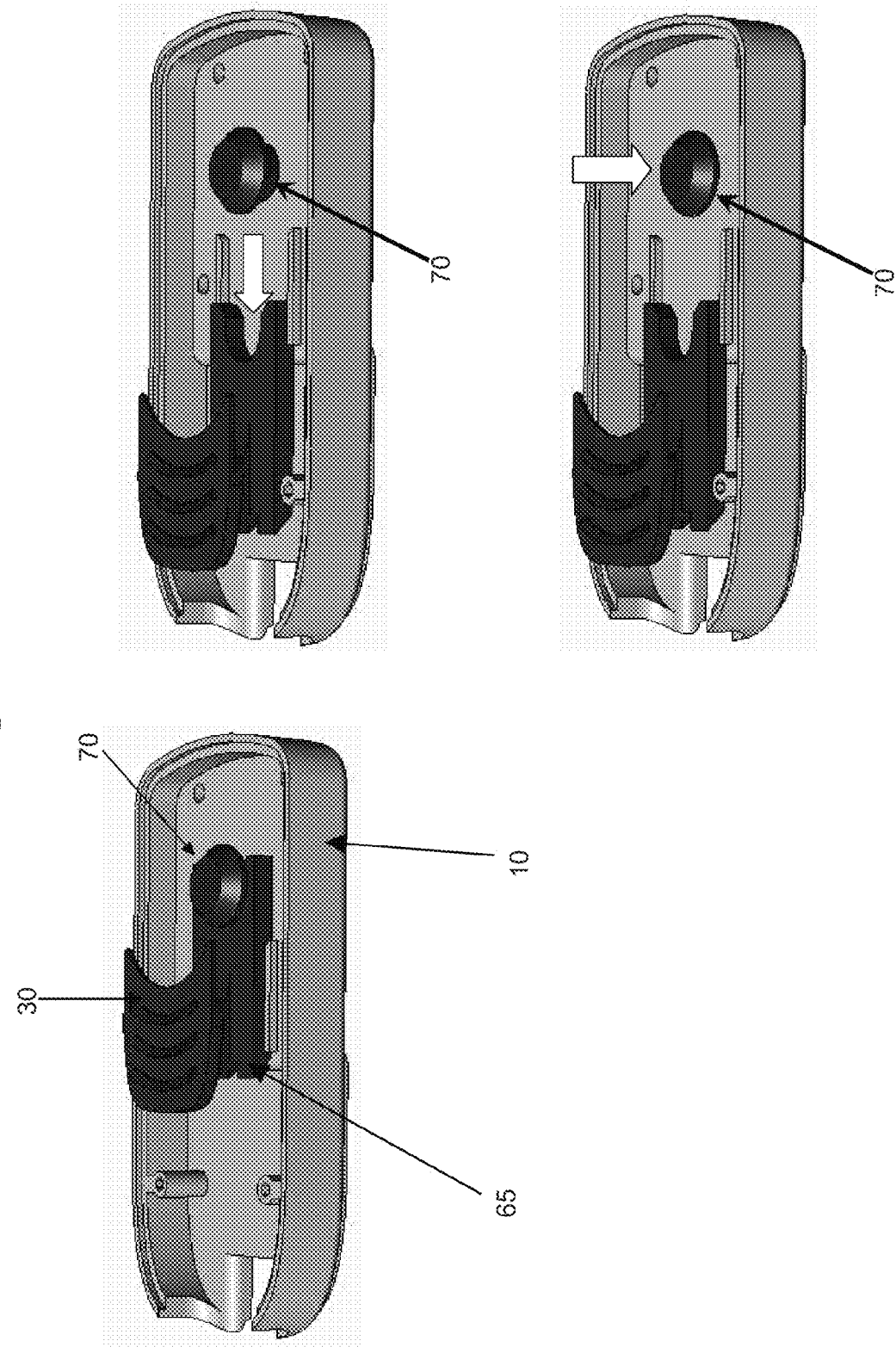
FIG. 5: Depicts some components of a representative device in various positions according to some embodiments of the present invention.

FIG. 5 depicts a partial view of a device comprising a first housing member (10), a locking member (65), a sliding button (30), and force member (70). FIG. 5 depicts the locking member (65) in contact with the force member (70) such that the force member (70) is in a raised method. FIG. 5 also depicts the movement of the locking member (65) and the sliding button (30) away from the force member (70) allowing the force member to change positions. In some embodiments, the change in position is that the force member is lowered.

Figure 6:
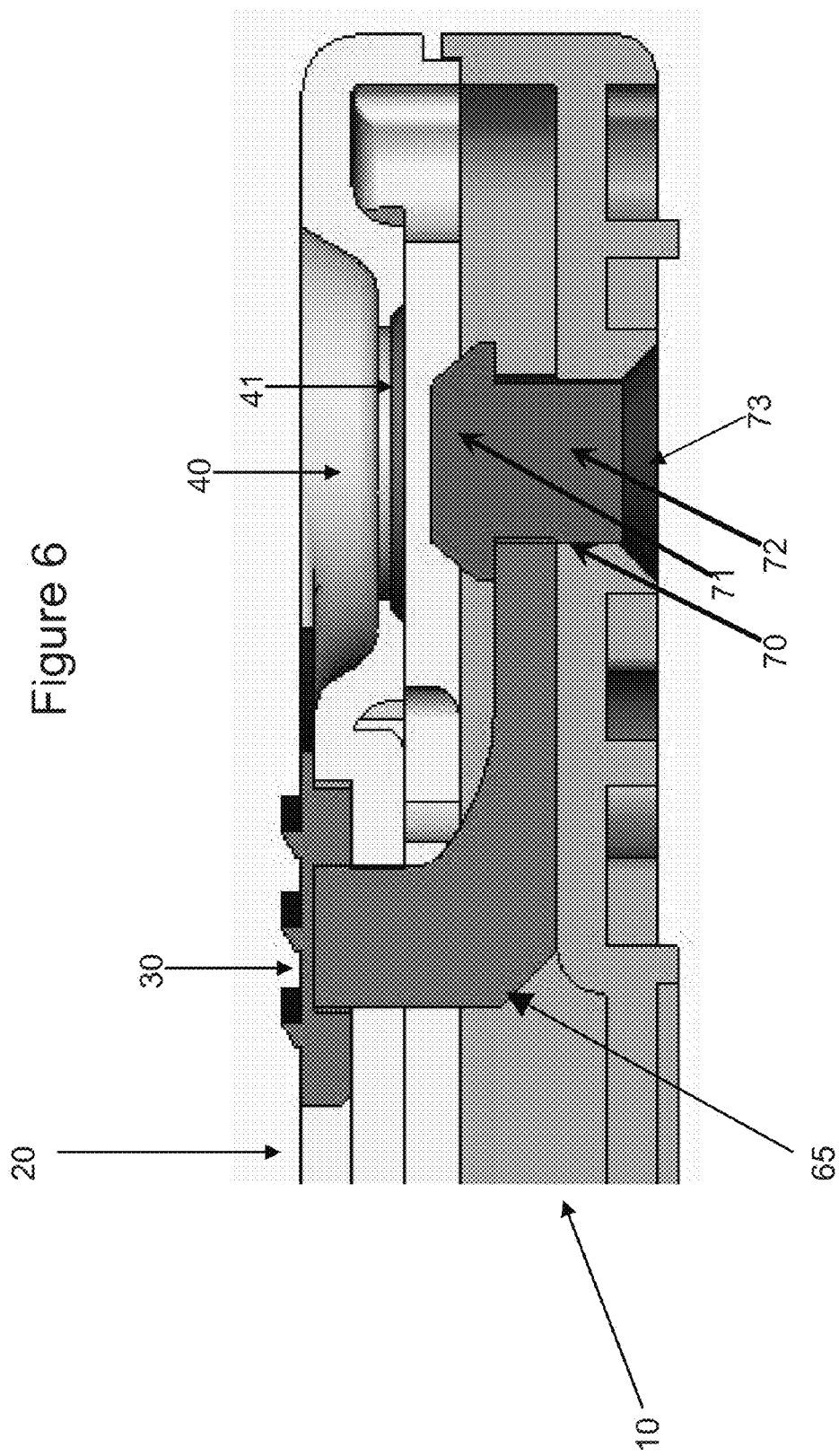
FIG. 6: Depicts a lateral view of some components of a representative device according to some embodiments of the present invention.

FIG. 6 depicts a side cut away view of a device comprising a first housing member (10), a second housing member (20), a sliding button (30), a locking member (65), a collar (40), an O-ring (41), a force member (70), and a support for the force member (73). The support for the shaft can be, for example, part of the first housing member (10) and is shaded differently for example purposes only. FIG. 6 depicts the button (30) in contact with the locking member (65) in such a way that movement of the button (30) will move the locking member (65). Movement of the locking member (65) will take away the support from the force member (70), which would allow the force member (70) to change positions. FIG. 6 also depicts the shaft (72) and the head (71) of the force member. The head (71) creates a lip where the locking member (65) can slide under and support the force member (70).

Figure 7:
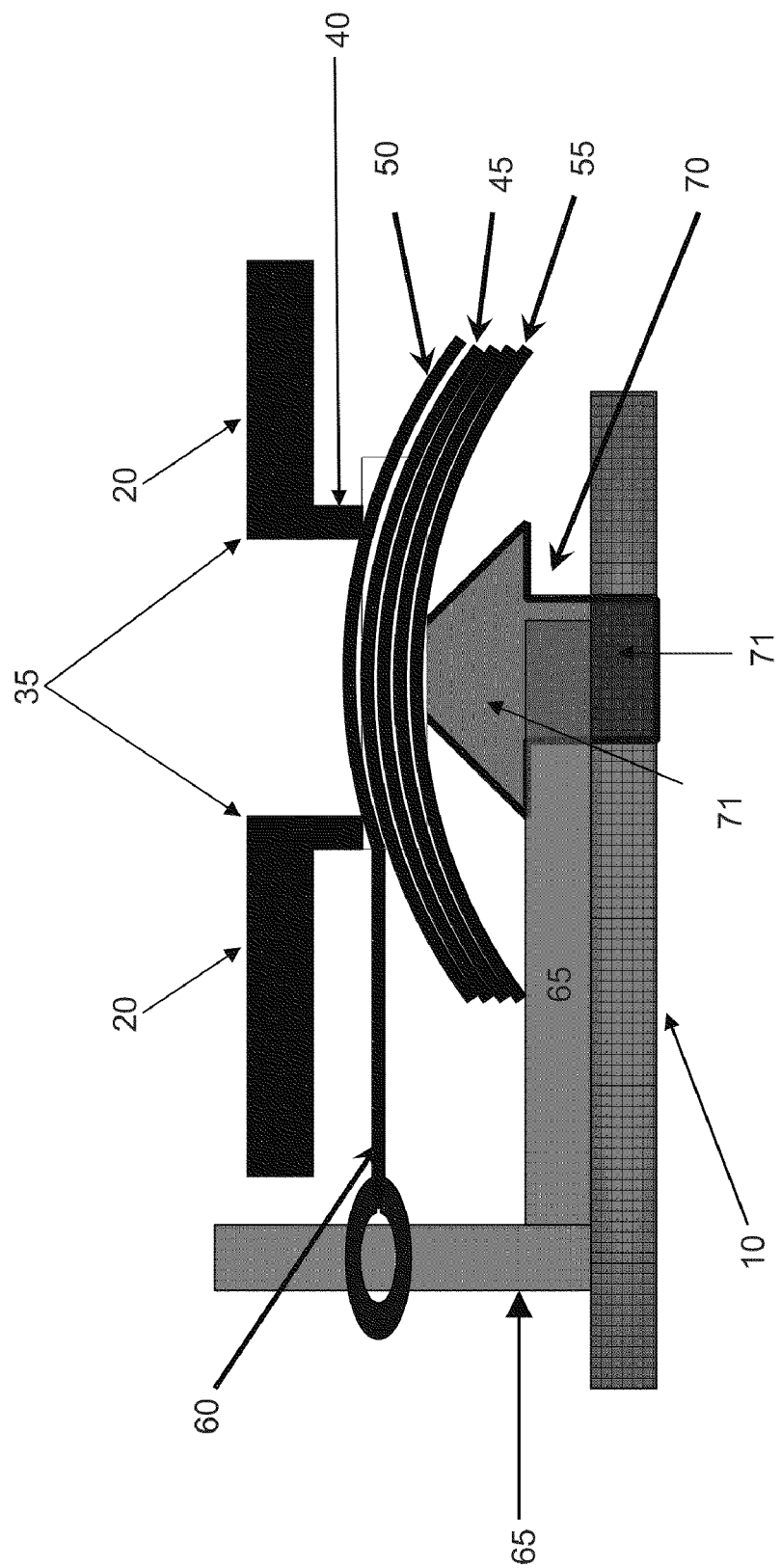
FIG. 7: Depicts a lateral view of some components of a representative device according to some embodiments of the present invention.
Figure 8:
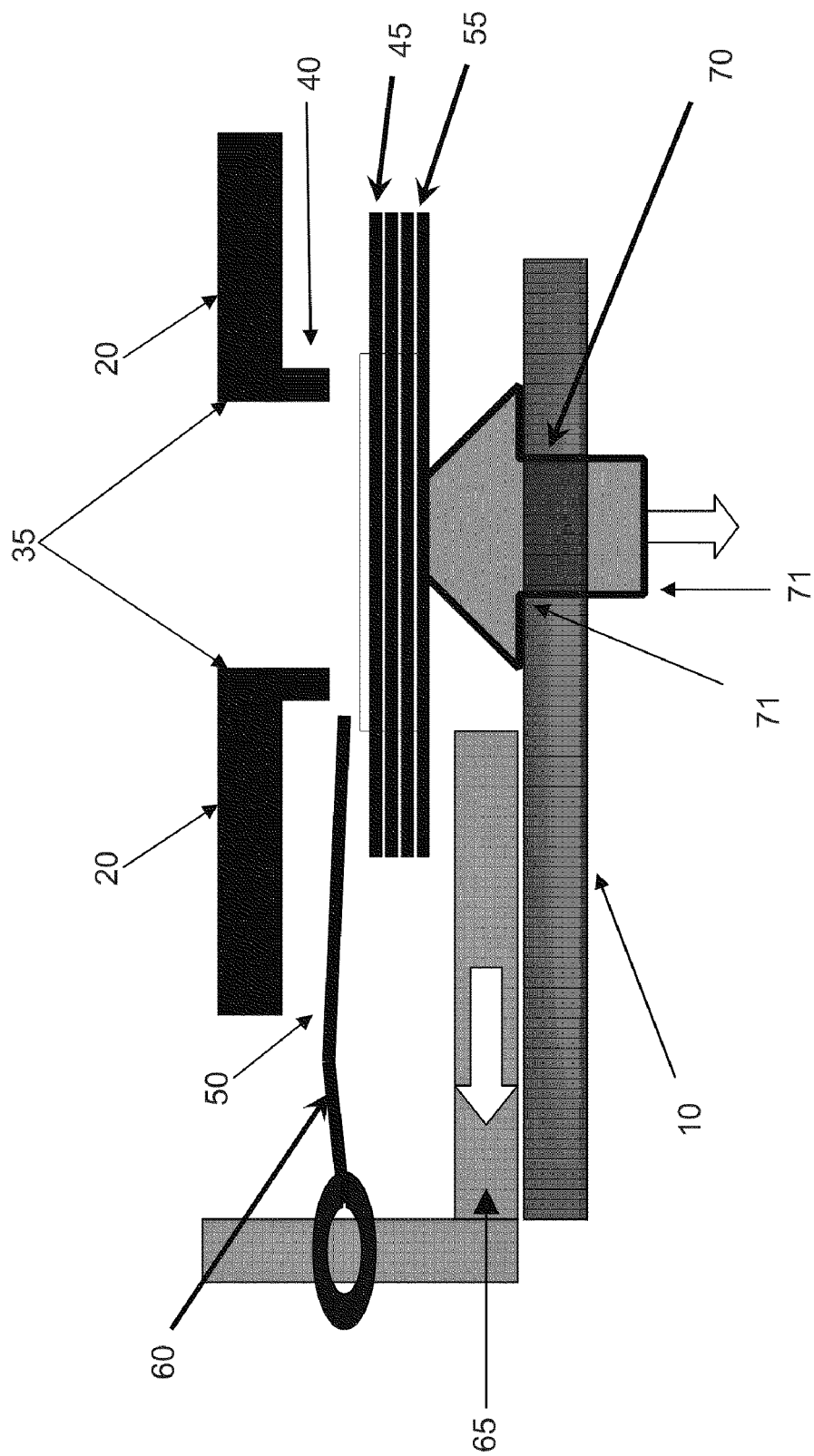
FIG. 8: Depicts a lateral view of some components of a representative device according to some embodiments of the present invention.
Figure 9:
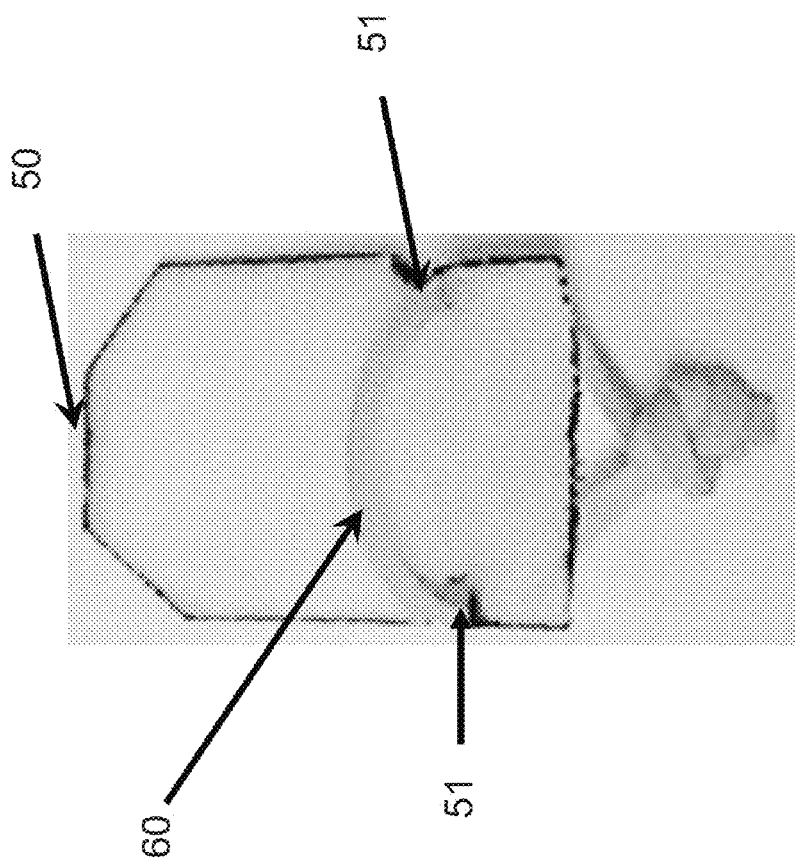
FIG. 9: Depicts a flexible attachment member attached to a conjugate pad.

FIG. 7 depicts a partial view of a device comprising a first housing member (10), a second housing member (20), an inlet opening (35), a test membrane (45), a conjugate pad (50), a plurality of absorbent members (55), an attachment member (60), a locking member (65), and a force member (70). FIG. 8 depicts the attachment member (60) attached to the conjugate pad (50) and the locking member (65). FIG. 8 also depicts the conjugate pad being compressed against the second housing member (20) and the perimeter of the inlet opening (35). FIG. 7 depicts the head of the force member (71) applying the pressure by contacting the plurality of absorbent members (55). In FIG. 9, a sample can be applied to the device through the inlet opening (35) so that the sample contacts the conjugate pad (50) and because of the pressure the sample through vertical flow contacts the test membrane (45).

FIG. 8 depicts a partial view of a device comprising a first housing member (10), a second housing member (20), an inlet opening (35), a test membrane (45), a conjugate pad (50), a plurality of absorbent members (55), an attachment member (60), a locking member (65), and a force member (70). FIG. 8 depicts the movement of the locking member (65), which is attached to the attachment member (60). The movement of the attachment member (60), which is attached to the conjugate pad (50) moves the conjugate pad. FIG. 8 depicts the test force member (70) changing positions and a lessening or elimination of the pressure and/or compression of the test membrane (45). FIG. 9 also depicts the movement of the conjugate pad (50) away from the inlet opening (35) revealing the test membrane (45) for visualization and/or detection.

FIG. 9 depicts an attachment member (60) attached to a conjugate pad (50). FIG. 9 depicts notches (51) in the conjugate pad (50) as locations for the attachment member (60) to attach to. The attachment member can also be attached through other means such as through adhesives, staples, and other forms of attachment.

Figure 10:
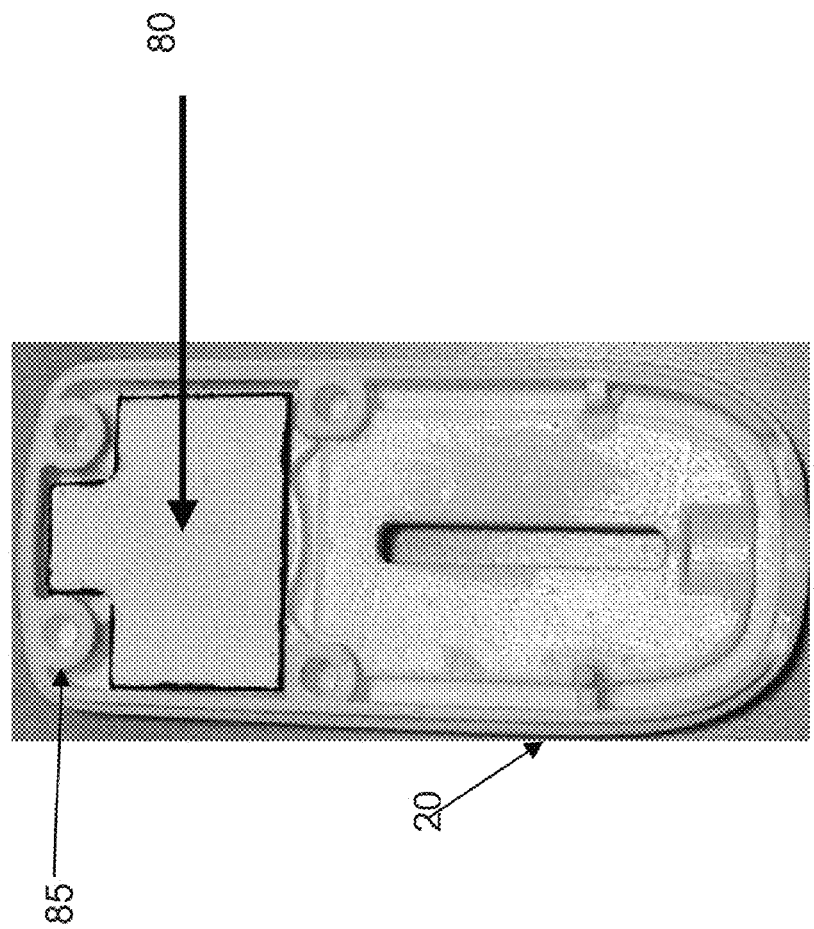
FIG. 10: Depicts membranes in a representative housing member.

FIG. 10 depicts a partial view of device comprising a second housing member (20), a plurality of pads or membranes (80), wherein the plurality of pads comprises a test membrane, a permeable membrane, and one or more absorbent members, and retaining members (85) that can retain the plurality of pads or membranes (80). FIG. 10 depicts the structures that when the conjugate pad is moved the plurality of pads remains in place. Any means or other structure can be used to keep the plurality of pads in place.

The invention is now described with reference to the following examples. These examples are provided for the purpose of illustration only and the invention should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Antibody specific for *E. coli* 0157:H7 conjugated to colloidal gold was baked and dried onto the conjugate pad. A second antibody specific for *E. Coli* 0157:H7 and an antiantibody was striped onto a test membrane and assembled into an antigen detection device.

A sample containing LPS *E. Coli* 0157 was serially diluted in PBS to concentrations of 100 g/ml, 50 g/ml, 25 g/ml, 12.5 g/ml, 6.25 g/ml, 3.125 g/ml, 1.56 µg/ml, and 0.78 µg/ml. The samples were applied to the device to detect the presence of LPS *E. Coli* 0157. The experiments were graded based upon signal intensity and the results are shown below. PBS was used as a negative control. TL refers to the test line (antigen specific) and CL refers to the control line (non-antigen specific). The detection occurred within 30 to 60 seconds of application of the sample onto the conjugate pad. The device could detect the presence of a food borne antigen.

| | Grade | |
|---|---|---|
| Sample Concentration | TL | CL |
| 100 ug/ml | 6 | 8 |
| 50 ug/ml | 6 | 8 |
| 25 ug/ml | 4 | 8 |
| 12.5 ug/ml | 4 | 8 |
| 6.25 ug/ml | 3 | 8 |
| 3.125 ug/ml | 3 | 8 |
| 1.56 ug/ml | 1 | 8 |
| 0.78 ug/ml | 1 | 8 |
| 1XPBS (Negative Control) | 1 | 8 |

The disclosures of each and every patent, patent application, publication, and accession number cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device for detecting a target molecule comprising:
   a housing comprising:
      an inlet opening in fluid contact with a conjugate pad;
      a force member;
      a slidable locking member contacting the force member;
      an attachment member contacting the force member;
      a sliding button contacting the attachment member; and
      a detection membrane system comprising the conjugate pad, a test membrane, and an absorbent member,
   wherein at least a portion of the conjugate pad, test membrane, and absorbent member are substantially parallel to each other,
   wherein the force member contacts the detection membrane system and is capable of applying pressure substantially perpendicular to the detection membrane system, and
   wherein the sliding button moves the slidable locking member.

2. The device of claim 1, wherein the attachment member contacts the conjugate pad.

3. The device of claim 1, wherein the detection membrane system further comprises a permeable membrane.

4. The device of claim 1, wherein the detection membrane system is compressed by the force member.

5. The device of claim 1, further comprising a hydrophobic membrane located between the test membrane and the absorbent member.

6. The device of claim 1, wherein the attachment member is a flexible attachment member.

7. The device of claim 1, wherein the conjugate pad comprises a first capture reagent that binds the target molecule.

8. The device of claim 7, wherein the first capture reagent is a first antigen-specific antibody.

9. The device of claim 7, wherein the target molecule is a polynucleotide, a peptide, a protein, a saccharide, or a carbohydrate.

10. The device of claim 8, wherein the first antigen-specific antibody is a polyclonal antibody, a monoclonal antibody, a chimeric antibody, an Fc fragment, or a single chain antibody.

11. The device of claim 7, wherein the target molecule is a pathogen protein or a fragment thereof.

12. The device of claim 7, wherein the target molecule is a food-borne pathogen target molecule.

13. The device of claim 12, wherein the food-borne pathogen target molecule is a polynucleotide.

14. The device of claim 7, wherein the target molecule is a food-borne pathogen antigen.

15. The device of claim 14, wherein the food-borne pathogen antigen is an antigen from an *E. coli* species, a *Campylobacter* species, *Listeria* species or a *Salmonella* species.

16. The device of claim 7, wherein the first capture reagent further comprises colloidal gold, a fluorescent molecule, a radioactive tag, an infrared molecule, or a chemiluminescent substrate.

17. The device of claim 1, wherein the conjugate pad comprises a plurality of capture reagents.

18. The device of claim 17, wherein the plurality of capture reagents is a plurality of antigen-specific antibodies.

19. The device of claim 18, wherein the plurality of antigen-specific antibodies bind to different antigens.

20. The device of claim 1, wherein the test membrane comprises a second capture reagent.

21. The device of claim 20, wherein the second capture reagent is an antigen-specific antibody.

22. The device of claim 20, wherein the target molecule is a target molecule from *E. coli, Campylobacter, Listeria*, or *Salmonella*.

23. The device of claim 1, wherein the test membrane comprises a plurality of capture reagents.

24. The device of claim 23, wherein the plurality of capture reagents binds to different target molecules.

25. The device of claim 24, wherein the plurality of capture reagents is a plurality of antigen-specific antibodies.

26. The device of claim 25, wherein the plurality of antigen-specific antibodies bind to different antigens.

27. The device of claim 1, wherein the test membrane comprises a plurality of areas comprising a plurality of capture reagents.

28. The device of claim 27, wherein the plurality of capture reagents bind to different target molecules, wherein the different target molecules are each independently chosen from *E. coli*, a *Campylobacter, Listeria*, and *Salmonella*.

29. The device of claim 1, wherein the housing comprises a first housing member and a second housing member.

30. A system comprising a device of claim 1 and a buffer container or a sample collector.

31. A kit comprising the device of claim 1 and one or more of a positive control, a negative control, an instruction booklet, a buffer container, or a sample collector.

32. A method of detecting a target molecule comprising:
contacting a sample with the conjugate pad of the device of claim 7, wherein the attachment member contacts the conjugate pad, wherein the sample vertically flows from the conjugate pad to the test membrane;
moving the conjugate pad after a portion of the sample has contacted and flowed through the conjugate pad, thereby exposing at least a portion of the test membrane for detection;
and
identifying a positive or negative reaction for the target molecule.

33. The method of claim 32, wherein the sample is contacted with the conjugate pad prior to compressing the detection membrane system.

34. The method of claim 32, wherein the conjugate pad is moved by moving the slidable locking member.

* * * * *